(12) United States Patent
Klein

(10) Patent No.: US 8,246,587 B2
(45) Date of Patent: *Aug. 21, 2012

(54) INFILTRATION CANNULA

(76) Inventor: Jeffrey A. Klein, San Juan Capistrano, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/037,756

(22) Filed: Mar. 1, 2011

(65) Prior Publication Data

US 2011/0152837 A1 Jun. 23, 2011

Related U.S. Application Data

(63) Continuation of application No. 11/646,043, filed on Dec. 27, 2006, now Pat. No. 7,914,504, which is a continuation of application No. 10/442,370, filed on May 21, 2003, now abandoned.

(51) Int. Cl.
*A61M 5/32* (2006.01)

(52) U.S. Cl. .................................. 604/264; 604/272

(58) Field of Classification Search .................. 604/35, 604/506, 187, 239, 272, 264, 542, 902, 246, 604/93.01

See application file for complete search history.

(56) References Cited

U.S. PATENT DOCUMENTS

| | | |
|---|---|---|
| 2,708,437 A | 5/1955 | Hutchins |
| 3,082,805 A | 3/1963 | Royce |
| 3,732,858 A | 5/1973 | Banko |
| 3,734,099 A | 5/1973 | Bender |
| 3,955,579 A | 5/1976 | Bridgman |
| 3,994,297 A | 11/1976 | Kopf |
| 4,167,944 A | 9/1979 | Banko |
| 4,203,444 A | 5/1980 | Bonnell et al. |
| 4,311,140 A | 1/1982 | Bridgman |
| 4,314,560 A | 2/1982 | Helfgott et al. |
| 4,405,322 A | 9/1983 | Jessup |
| 4,460,360 A | 7/1984 | Finegold |
| 4,487,600 A | 12/1984 | Brownlie et al. |

(Continued)

FOREIGN PATENT DOCUMENTS

FR 2777462 10/1999

OTHER PUBLICATIONS

Jeffrey Alan Klein, MD; The Tumescent Technique Anesthesia and Modified Liposuction Technique Dermatologic Clinic; vol. 8, No. 3, Jul. 1990.

(Continued)

*Primary Examiner* — Laura Bouchelle
(74) *Attorney, Agent, or Firm* — Stetina Brunda Garred & Brucker

(57) ABSTRACT

An infiltration cannula and method of using the infiltration cannula during an infiltration procedure are disclosed herein. The infiltration cannula includes: a tubular needle and a hub. The tubular needle has a proximal end and a distal end. The tubular needle also has a plurality of apertures disposed in a pattern about the distal end. The apertures are configured to infiltrate fluid into the subcutaneous tissue of a patient. The hub is configured to be held by a person performing the infiltration procedure. The hub has a first end and an opposing second end. The first end is attached to the proximal end of the tubular needle and the second end includes a connector configured to connect to an input source for receiving the fluid to be infiltrated into the subcutaneous tissue of the patient. The fluid flows from the connector, through the hub and into the tubular needle.

4 Claims, 3 Drawing Sheets

U.S. PATENT DOCUMENTS

| | | |
|---|---|---|
| 4,530,356 A | 7/1985 | Helfgott et al. |
| 4,536,180 A | 8/1985 | Johnson |
| 4,577,629 A | 3/1986 | Martinez |
| 4,586,921 A | 5/1986 | Berson |
| 4,589,414 A | 5/1986 | Yoshida et al. |
| 4,713,053 A | 12/1987 | Lee |
| 4,735,605 A | 4/1988 | Swartz |
| 4,775,365 A | 10/1988 | Swartz |
| 4,784,649 A | 11/1988 | Imonti et al. |
| 4,790,830 A | 12/1988 | Hamacher |
| 4,815,462 A | 3/1989 | Clark |
| 4,850,354 A | 7/1989 | McGurk-Burleson et al. |
| 4,886,491 A | 12/1989 | Parisi et al. |
| 4,919,129 A | 4/1990 | Weber, Jr. |
| 4,925,450 A | 5/1990 | Imonti et al. |
| 4,932,935 A | 6/1990 | Swartz |
| 4,938,743 A | 7/1990 | Lee |
| 5,052,999 A | 10/1991 | Klein |
| 5,112,302 A | 5/1992 | Cucin |
| 5,181,907 A | 1/1993 | Becker |
| 5,186,714 A | 2/1993 | Boudreault et al. |
| 5,203,769 A | 4/1993 | Clement et al. |
| 5,236,414 A | 8/1993 | Takasu |
| 5,242,386 A | 9/1993 | Holzer |
| 5,244,458 A | 9/1993 | Takasu |
| 5,286,253 A | 2/1994 | Fucci |
| 5,295,980 A | 3/1994 | Ersek |
| 5,314,407 A | 5/1994 | Auth |
| 5,348,535 A | 9/1994 | Cucin |
| 5,352,194 A | 10/1994 | Greco |
| 5,446,070 A | 8/1995 | Mantelle |
| 5,447,493 A | 9/1995 | Blugerman et al. |
| 5,453,088 A | 9/1995 | Boudewiin et al. |
| 5,472,416 A | 12/1995 | Blugerman et al. |
| 5,489,291 A | 2/1996 | Wiley |
| 5,514,086 A | 5/1996 | Parisi |
| 5,643,198 A | 7/1997 | Cucin |
| 5,655,544 A | 8/1997 | Johnson |
| 5,725,495 A | 3/1998 | Strukel et al. |
| 5,795,323 A | 8/1998 | Cucin |
| 5,800,407 A | 9/1998 | Eldor |
| 5,807,282 A | 9/1998 | Fowler |
| 5,817,050 A | 10/1998 | Klein |
| 5,884,631 A | 3/1999 | Silberg |
| 5,947,988 A | 9/1999 | Smith |
| 5,968,008 A | 10/1999 | Grams |
| 6,020,196 A | 2/2000 | Hu et al. |
| 6,039,048 A | 3/2000 | Silberg |
| 6,071,260 A | 6/2000 | Halverson |
| 6,102,885 A | 8/2000 | Bass |
| 6,113,569 A | 9/2000 | Becker |
| 6,129,701 A | 10/2000 | Cimino |
| 6,162,202 A | 12/2000 | Sicurelli et al. |
| 6,238,355 B1 | 5/2001 | Daum |
| 6,280,424 B1 | 8/2001 | Chang et al. |
| 6,375,648 B1 | 4/2002 | Edelman et al. |
| 6,428,499 B1 | 8/2002 | Halverson |
| 6,436,116 B1 | 8/2002 | Spitz et al. |
| 6,524,300 B2 | 2/2003 | Meglin |
| 6,613,026 B1 | 9/2003 | Palasis et al. |
| 6,685,666 B1 | 2/2004 | Fontenot |
| 6,692,473 B2 | 2/2004 | St. Cyr et al. |
| 6,706,026 B1 | 3/2004 | Goldstein et al. |
| 6,916,292 B2 | 7/2005 | Morawski et al. |
| 6,969,373 B2 | 11/2005 | Schwartz et al. |
| 7,056,315 B2 | 6/2006 | Gonon |
| 7,465,291 B2 | 12/2008 | Massengale |
| 7,914,504 B2 * | 3/2011 | Klein .................. 604/264 |
| 2004/0215143 A1 | 10/2004 | Brady et al. |
| 2004/0236313 A1 | 11/2004 | Klein |
| 2006/0259111 A1 | 11/2006 | Peterson et al. |

OTHER PUBLICATIONS

Jeffrey A. Klein, M.D.; "The Tumescent Technique for Lipo-Suction Surgery", The American Journal of Cosmetic Surgery; vol. 4, No. 4, 1987.

Jeffrey A. Klein, M.D.; "Tumescent Technique for Regional Anesthesia Permits Lidocaine Doses of 35 mg/kg for Liposuction"; J. Dermatol. Surg. Oncol 16:3; Mar. 1990.

Jeffrey A. Klein, M.D.; "Tumescent Technique for Local Anesthesia Improves Safety in Large-Volume Lipsuction"; The American Society of Plastic and Reconstructive Surgeons; Nov. 1993.

Website: www.greer-medical.com; Greer Medical, Inc., SeromaCath Wound Drainage System (4 pages), Apr. 19, 2004.

Axiom Medical, Inc. SeroVac II and SeroVac Series drainage products (2 pages), May 11, 2004.

Greer Medical, Inc., SeromaCath Wound Drainage System pamphlet and instructions for use. (3 pages), May 24, 2011.

"Patient-Controlled Transdermal Fentanyl Hydrochloride vs. Intravenous Morphine Pump for Postoperative Pain" article in JAMA, Mar. 17, 2004-vol. 291, No. 11 (9 pages).

* cited by examiner

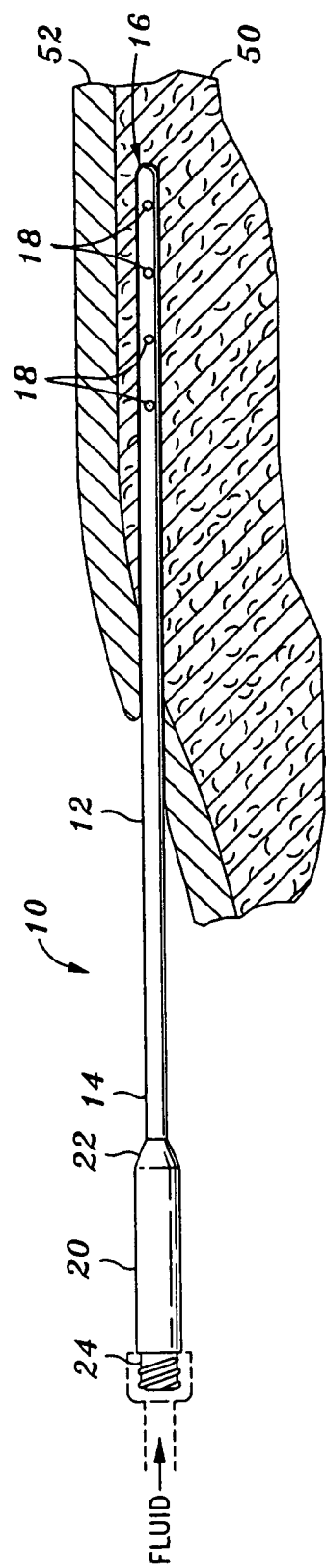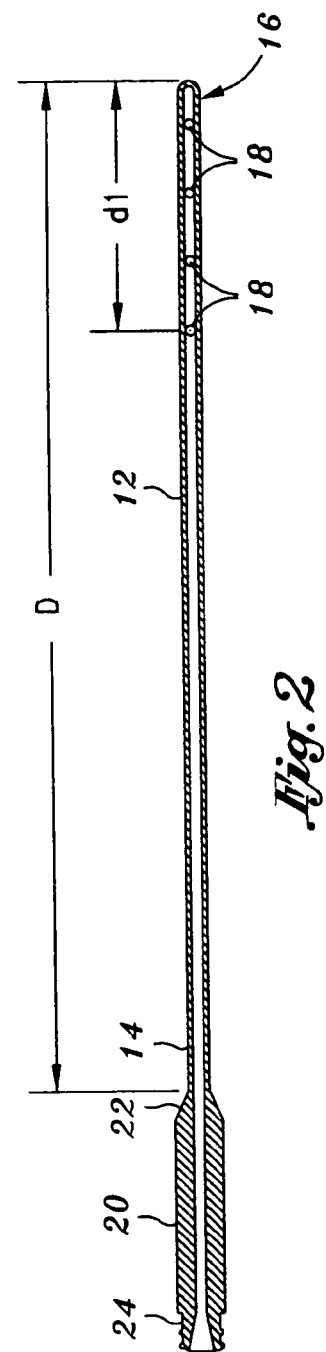

INFILTRATION CANNULA

CROSS-REFERENCE TO RELATED APPLICATIONS

The present application is a continuation of U.S. patent application Ser. No. 11/646,043 filed on Dec. 27, 2006 now U.S. Pat. No. 7,914,504 which is a continuation of U.S. patent application Ser. No. 10/442,370 filed on May 21, 2003 now abandoned, the entirety of the disclosures of which are expressly incorporated herein by reference.

STATEMENT RE: FEDERALLY SPONSORED RESEARCH/DEVELOPMENT

Not Applicable

BACKGROUND OF THE INVENTION

The present invention relates in general to cannulas and in particular to an infiltration cannula that allows for intermittent infiltration of fluids, such as a local anesthetic.

Many medical procedures require infiltration of fluids, such as a local anesthetic. One method of infiltration of local anesthetic is via an infiltration cannula. Infiltrators currently on the market are known as sprinkler-tip or Klein (the present applicant) needle infiltrators. These cannulas are constructed out of a rigid stainless steel and have one or more apertures, which are typically round or oval, and are distributed about the distal end of the cannula. The apertures are distributed over about 15% to 25% or less than 5.0 cm. of the distal end of the cannula needle. These traditional infiltration cannulas are intended to be inserted through a small incision in the patient's skin and then moved in and out through the subcutaneous tissue while a dilute solution of local anesthetic (or other pharmaceutical solution) is ejected through the distal apertures. Such infiltrators typically have a blunt tip and require the placement of a small hole (made by a one mm skin-biopsy punch or a small surgical blade) through which the blunt tipped cannula can be passed. The piston-like in and out motion of the cannula causes the patient discomfort.

Another method of fluid insertion is via a peripherally inserted central catheter, also called a PICC line comprising an elongate plastic tube that is placed inside a vein of the patient. PICC lines are typically used for procedures requiring delivery of fluids over a prolonged period of time. For example, a PICC line may be used when a patient needs to receive intravenous (IV) fluids, such as medication or nutrients over a prolonged period of time, such as a week or more.

The On-Q® Pain Management System marketed by I-Flow® Corporation employs a PICC line type system for continuously providing local anesthetic. This system provides prolonged local anesthesia by means of an elastomer (elastic container) device that continuously infiltrates a solution of local anesthesia over many hours. The On-Q® device is a long soft flexible tube with many small holes arranged along a significant portion of the tube. The On-Q® device is designed to be positioned within a surgical wound at the time of surgery; after the surgical wound is closed the On-Q® device permits slow steady infiltration of a local anesthetic solution into the wound, thereby attenuating post-operative pain. The On-Q® device cannot be inserted through a tiny hole in the skin into subcutaneous tissue. Thus there is a need for a simple device that can permit the direct percutaneous insertion of a multi-holed infiltration cannula into subcutaneous tissue for the localized delivery of medications such as local anesthetics, chemotherapeutic agents, or crystalloids for parenteral hydration.

Traditional techniques for subcutaneous injection of local anesthetic solutions use a high-concentration/low-volume of local anesthetic. This is associated with a rapid systemic absorption of the local anesthetic. In order to achieve a prolonged local anesthetic effect, the traditional techniques for using local anesthetics necessitate either frequent repeated injections or slow continuous subcutaneous infusion of the local anesthetic. As described above, repeated injections or piston-like movement of the cannula causes patient discomfort. Slow continuous infiltration may not be desirable in certain situations. Furthermore, continuous infiltrations restrict patient movement for extended periods of time which also cause the patient discomfort. Thus, there is a need for a system for infiltration of a local anesthetic into subcutaneous tissue which decreases patient discomfort, and allows prolonged local anesthesia.

BRIEF SUMMARY OF THE INVENTION

An infiltration cannula and method of using the infiltration cannula during an infiltration procedure are disclosed herein. The infiltration cannula includes: a tubular needle and a hub. The tubular needle has a proximal end and a distal end. The tubular needle also has a plurality of apertures disposed in a pattern about the distal end. The apertures are configured to infiltrate fluid into the subcutaneous tissue of a patient. The hub is configured to be held by a person performing the infiltration procedure. The hub has a first end and an opposing second end. The first end is attached to the proximal end of the tubular needle and the second end includes a connector configured to connect to an input source for receiving the fluid to be infiltrated into the subcutaneous tissue of the patient. The fluid flows from the connector, through the hub and into the tubular needle.

The tubular needle may be manufactured of stainless steel or plastic.

The apertures may be arranged in a helical pattern or in a spiral pattern.

The apertures may be distributed over about 33% to about 90% of the distal end of the tubular needle.

The apertures may be round or oval.

The fluid may be a local anesthetic.

The infiltration procedure may be performed in conjunction with a liposuction procedure.

A method of infiltrating fluid into subcutaneous tissue of a patient using an infiltration cannula, such as the one described above may include the following steps: (1) inserting an infiltration cannula through a patient's skin and into the subcutaneous tissue of the patient at a desired site; (2) receiving fluid from the fluid source via the connector; (3) transporting the fluid from the connector through the hub and into the tubular needle; and (4) ejecting the fluid from the tubular needle into the subcutaneous tissue of the patient via the apertures. The infiltration cannula used in performing the method includes: a connector for receiving the fluid from a fluid source, a hub in communication with the connector and a tubular needle in communication with the hub. The tubular needle has a plurality of apertures disposed in a pattern about a distal end. The apertures are configured to infiltrate the fluid into the subcutaneous tissue of the patient.

Steps (1)-(4) may be repeated intermittently. The steps may be repeated at intervals between about eight hours and twelve hours.

After the desired amount of fluid has been infiltrated at a given site, the infiltration cannula is removed.

The infiltration cannula may be inserted at a new site.

Multiple infiltration cannulas (e.g., two) may be used simultaneously. Use of multiple infiltration cannulas prevents disruption of the method infiltration process when one infiltration cannula is removed.

BRIEF DESCRIPTION OF THE DRAWINGS

These as well as other features of the present invention will become more apparent upon reference to the drawings wherein:

FIG. 1 is a side elevation view of a stainless steel infiltration cannula shown inserted in subcutaneous tissue shown in partial cross section;

FIG. 2 is a section view of the infiltration cannula shown in FIG. 1;

DETAILED DESCRIPTION OF THE INVENTION

As described in further detail below, the present invention takes advantage of the tumescent technique in order to provide intermittent infiltration of local anesthetic. The present invention results in a significant decrease in patient discomfort due to the elimination of the piston-like in and out motion of the cannula. Once the cannula is in place, there is no need to push the cannula through the tissue in order to deliver the fluid to a wide area. Using the tumescent technique, the time needed in order to complete the infiltration of a targeted anatomic area is reduced to nearly half of the time required when using traditional prior art cannulas. The device and method described herein can use multiple (e.g., two) infiltration cannulas simultaneously. While one cannula is actively dispersing tumescent fluid into the subcutaneous tissue, the surgeon can reposition a second infiltration cannula. This allows the infiltration process to proceed without interruption, whereas prior art techniques of infiltration must be ceased each time the cannula is withdrawn from the skin and re-inserted into another direction.

The tumescent technique was discovered by Jeffrey Alan Klein, M.D. (the applicant) in 1985. Dr. Klein first published a description of the tumescent technique in 1987 when he described the use of dilute lidocaine and epinephrine to permit liposuction totally by local anesthesia. A detailed description of the tumescent technique has not been published in anesthesiology literature, and therefore, the unique benefits of the tumescent technique are not well recognized by anesthesiologists.

The tumescent technique is a drug delivery system that takes advantage of a recently discovered reservoir effect of injecting a relatively large volume of relatively dilute solution of a drug into the subcutaneous tissue.

The present invention takes advantage of the tumescent reservoir phenomenon. It has many novel applications, an example of which is pain management. This technique eliminates the need for a continuous infiltration of local anesthetic and allows for intermittent injections. In exemplary embodiments, the intermittent injections are administered every eight to twelve hours.

With the tumescent technique, a large volume of dilute solution of local anesthesia and epinephrine is injected into the subcutaneous space resulting in a large bolus (or reservoir) of solution. The profound vasoconstrictive effect (shrinking of the capillaries) of the dilute epinephrine produces a dramatic delay in the systemic absorption of the local anesthetic, which prolongs the anesthetic effects of tumescent anesthesia for eight to sixteen times longer than traditional techniques.

Figure 3:
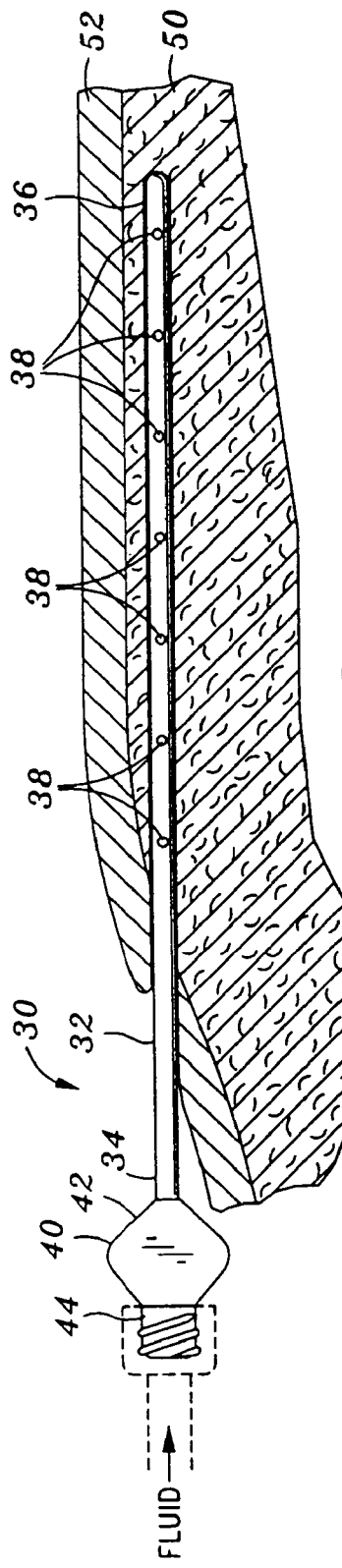
FIG. 3 is a side elevation view of a plastic infiltration cannula shown inserted in subcutaneous tissue shown in partial cross section.
Figure 4:
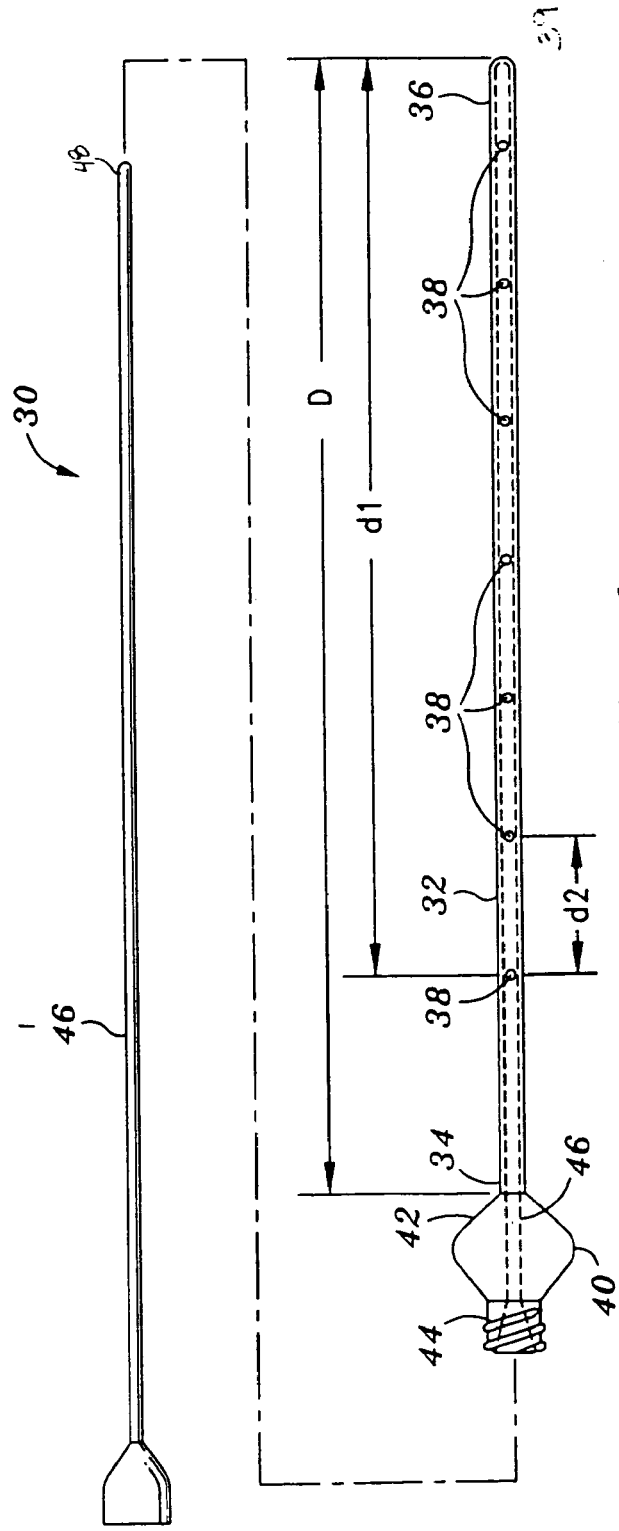
FIG. 4 is an exploded view of the infiltration cannula shown in FIG. 3.

Referring now to the drawings wherein the showings are for purposes of illustrating preferred embodiments of the present invention only, and not for purposes of limiting the same, FIGS. 1 and 2 illustrate a stainless steel (reusable) infiltration cannula 10 and FIGS. 3-4 illustrate a (single use) plastic infiltration cannula 30. The cannula 10, 30 can be inserted under the skin 52 and into the subcutaneous tissue 50 and tumescent local anesthesia can be infiltrated once every eight to twelve hours.

Stainless steel infiltration cannulas 10, such as the one shown in FIGS. 1 and 2, are precision high quality and reusable. These cannulas can be used to provide tumescent local anesthesia for surgical procedures, such as liposuction, which require tumescent local anesthesia over a relatively large area.

The cannula 10 includes a tubular needle portion 12 which has a proximal end 14 and a distal end 16. The proximal end 14 of the tubular needle 12 is attached to a hub 20 that is used by the anesthesiologist or surgeon to hold the cannula 10 during the infiltration procedure. The hub 20 is connected to the tubular needle 12 at a first end 22 and has a connector 24, such as a luer lock, at an opposing second end. The connector 24 is connected to a fluid source, such as tubing connected to an IV bag. Fluid enters the cannula 10 via the connector 24.

In exemplary embodiments, the tip at the distal end 16 is closed. The local anesthetic is infiltrated into the patient via apertures 18 located proximate the distal end 16 of the tubular needle 12 of the cannula 10. In exemplary embodiments, the apertures 18 are disposed along the distal end 16 of the cannula 10 in a spiral or helical pattern and are distributed over the distal 33% to 90% of the tubular needle 12 of the cannula 10. For example, if the length of the tubular needle 12 is 15 cm and the apertures 18 at the distal end 16 cover a length d1 of 5 cm, the pattern of apertures of the cannula 10 are distributed over 33% of the tubular needle 12 of the cannula 10.

The proximal portion 14 of the cannula 10 is devoid of apertures, in order to prevent fluid from leaking out of the cannula insertion site in the skin.

Plastic infiltration cannulas 30, such as the one shown in FIGS. 3 and 4, are single use cannulas and can be used in one of several unique ways. First, an anesthesiologist or surgeon can insert an infiltration cannula 30 with stylet 46 into the subcutaneous tissue 50, remove the stylet 46, then attach an IV tubing to the infiltrator and inject tumescent local anesthesia into the targeted area without subsequent repositioning of the infiltration cannula 30. The plastic flexible nature of the tubular needle 32 of the disposable plastic cannula 30 allows the patient to move or change position of the body without risk of injury that might result if a patient moves while a rigid steel cannula is inserted.

Preferably, the stylet 46 is metal, e.g., stainless steel. The plastic cannula 30 can be blunt-tipped with the metal stylet tip 48 covered by the rounded tip 39 of the plastic cannula 30. Alternatively, the plastic cannula 30 can be open-ended with the stylet 46 extending a short distance past the end 39 of the plastic cannula. 30. In the case of an open-ended cannula, the metal stylet 46 can be either blunt-tipped (requiring a skin incision to permit insertion into the subcutaneous space), or sharp-tipped (permitting the cannula to be inserted directly through the skin and into the subcutaneous space without requiring a preparatory skin incision.

The plastic cannula shown in FIGS. 3 and 4 is similar to an IV catheter except the sharp hollow stylet used for the insertion of an IV catheter is replaced by a solid obturator/stylet 46 that can be either sharp or blunt tipped. Except for the removable stylet 46, the plastic cannula 30 is similar to the stainless steel cannula 10 shown in FIGS. 1 and 2 and described above. The plastic cannula 30 includes a flexible tubular needle 32 having a proximal end 34 and a distal end 36. The distal end has apertures 38 and the proximal end 34 is devoid of apertures. As stated above, in exemplary embodiments, the pattern of apertures 38 in the cannula 30 are distributed over the distal 33% to 90% of the tubular needle 32 of the cannula 30. For example, if the tubular needle 32 of cannula 30 shown in FIGS. 3 and 4 has a length D of 15 cm and the pattern of apertures are distributed over a length d1 of 13.5 cm, then the apertures 38 are distributed over 90% of the cannula.

A typical infiltration cannula 10, 30 might be 20, 18, 16 or 14 gauge (i.e., 20, 18, 16 or 14 cm in length) with small apertures 18, 38 placed every 5 mm d2 along the cannula in a spiral or helical pattern. It will be appreciated that the dimensions used herein are exemplary and that the cannula dimensions, range of gauge, relative size shape and pattern of apertures can vary greatly depending upon clinical preference.

The proximal end 34 of the tubular needle 32 shown in FIGS. 3 and 4 is attached to a hub 40 that is used by the anesthesiologist or surgeon to hold the cannula 30 during the infiltration procedure. The hub 40 is connected to the tubular needle 32 at a first end 42 and has a connector 44 at an opposing second end. The connector 44 is connected to a fluid source. As described above and shown in FIG. 4, the stylet 46 can be inserted and removed from the cannula 30.

Infiltration using a plastic infiltration cannula 30, such as the one shown in FIGS. 3 and 4, can be accomplished using an infiltration pump. Alternatively, the force of gravity could be used to push the tumescent fluid into the tissues by hanging a reservoir plastic bag of tumescent local anesthesia (or other dilute drug, such as a chemotherapeutic agent or antibiotics) on an IV pole and connecting bag to the infiltration cannula by an IV line.

Another application is the injection of tumescent local anesthesia into a localized area through which a surgeon plans to make a surgical incision. The effects of vasoconstriction within the tumesced tissue minimizes surgical bleeding. The effects of tumescent local anesthesia produce prolonged post operative analgesia and also reduce the risk of surgical wound infections.

Yet another application is to provide an easily accessible route for systemic administration of crystalloid fluids/electrolytes for systemic hydration or for other types of drug therapy. Potential clinical applications include emergency resuscitation with systemic fluids in situations where insertion of an IV catheter into a vein cannot be readily achieved. Examples of situations where emergency access for intravenous delivery of fluids might not be possible include acute trauma or burn wound in civilian or military situations. Another application might be the emergency treatment of dehydration associated with prolonged vomiting or diarrhea (e.g., epidemic cholera) such as among pediatric patients in rural (e.g., third world) settings. A subcutaneous infiltration catheter can easily be placed by a layman, whereas inserting an IV catheter into a patient that is severely dehydrated can be difficult even for a skilled physician. Delivery of systemic fluids by subcutaneous infiltration is safer in a zero gravity situation (for example, the Space Station). The addition of a small amount of capillary vasodilator (e.g., methylnicotinamide) to the subcutaneous fluid can be used to accelerate the systemic absorption of the fluid or drug into the intravascular space.

The cannula 10, 30 is intended to be inserted far enough through the skin 52 so that all of the apertures 18, 38 are within the fat 50 of the patient. Once the cannula 10, 30 is properly positioned, it can remain stationary while the local anesthetic (or other pharmaceutical) solution is injected.

After one portion of the targeted area has been tumesced, the infiltration is briefly terminated (either by turning off the pump or by clamping the IV tubing) while the cannula 10, 30 is repositioned into another area of the subcutaneous tissue. The infiltration is then restarted with the cannula stationary in its new position.

The infiltrator 10, 30 can also be used in the traditional mode whereby the cannula 10, 30 is moved through the targeted tissue while the fluid is simultaneously pumped through the cannula 10, 30 and into the subcutaneous tissue 50.

Another unique aspect of the tumescent technique's reservoir effect is that one can conveniently achieve a long slow steady absorption of a drug delivered to the subcutaneous space 50 using periodic injections of a tumescent solution. In certain situations, using a slow IV infusion, the alternative technique, can achieve a slow systemic absorption of a drug but may be difficult, require greater clinical expertise, be more expensive, and therefore, less practical than the technique described herein.

Figure 5:
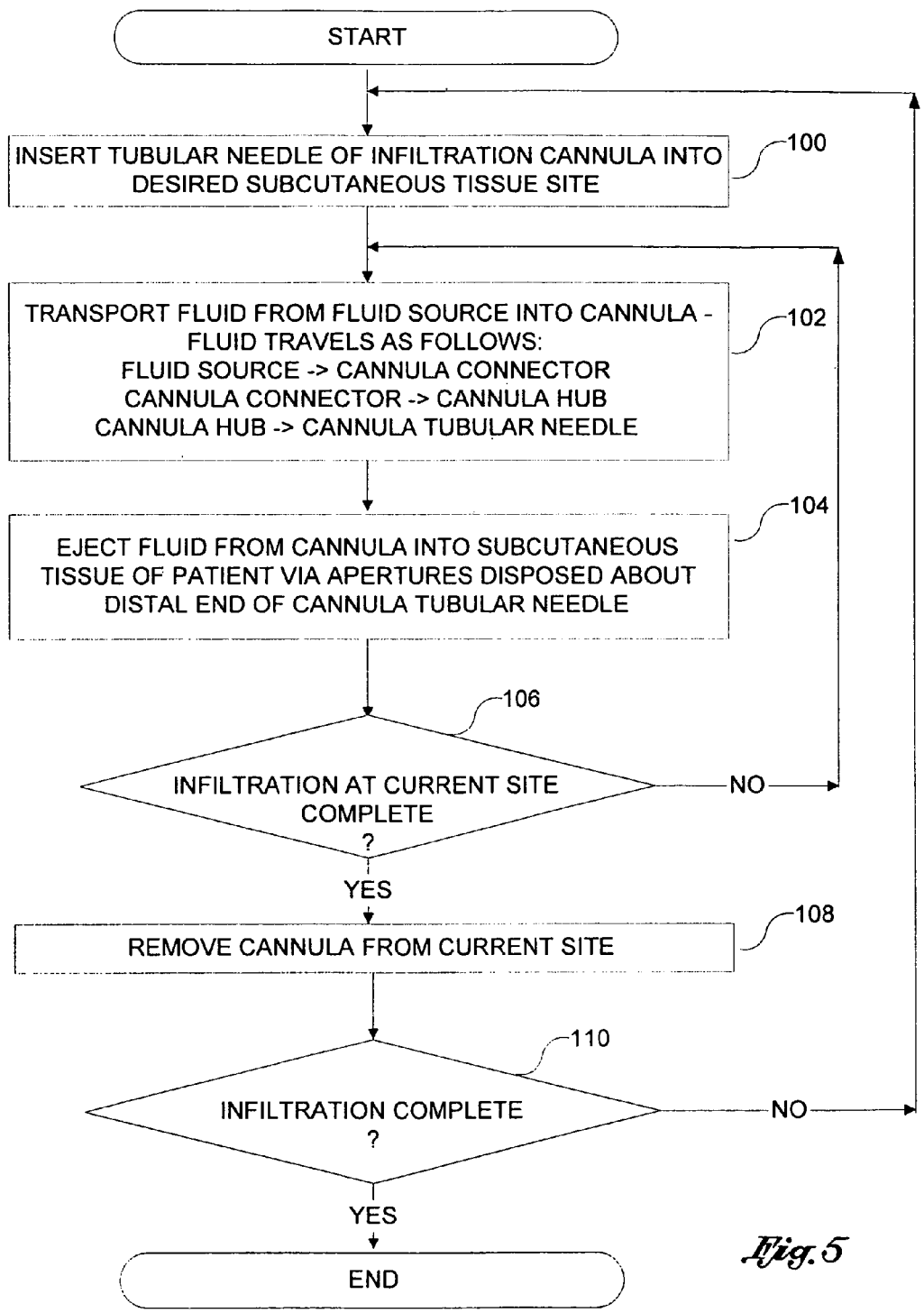
FIG. 5 is a flow diagram illustrating an exemplary procedure for using an infiltration cannula such as the one shown in FIG. 1 or the one shown in FIG. 3.

FIG. 5 is a flow diagram illustrating steps performed in an exemplary infiltration procedure using a cannula 10, 30 such as the one shown in FIGS. 1 and 2 or the one shown in FIGS. 3 and 4, respectively. The procedure begins by inserting the tubular needle 12, 32 of the infiltration cannula 10, 30 into a desired subcutaneous tissue site 50, e.g., via an incision in the patient's skin 52 (block 100). Fluid is then transported from the fluid source (e.g., an IV bag) into the cannula 10, 30 via the connector 24, 44 that is connected to the fluid source. The fluid is transported from the connector 24, 44 through the hub 20, 40 and into the tubular needle 12, 32 (block 102). The fluid is then ejected from the cannula 10, 30 into the subcutaneous tissue 50 of the patient via the apertures 18, 38 at the distal end 16, 36 of the tubular needle 12, 34 of the cannula 10. 30 (block 104).

The fluid is transported (block 102) and ejected (block 104) until infiltration at the current site is completed (yes in decision block 106). The fluid can be injected into multiple sites in order to distribute the solution over a greater area.

Infiltration at a particular site may be deemed complete upon emptying of the fluid source or based on the anesthesiologist or surgeon's decision to stop the infiltration at the current site. After one portion of the targeted area has been tumesced, the infiltration can be briefly terminated (either by turning off the pump or by clamping the IV tubing) while the cannula 10, 30 is repositioned into another area of the subcutaneous tissue. The infiltration is then restarted with the cannula stationary in its new position. If the infiltration at a site is complete (yes in decision block 106), the cannula is removed from the current site (block 108). If the infiltration at the current site is not complete (no in decision block 106), fluid is transported from the fluid source (block 102) and ejected into the subcutaneous tissue (block 104) until infiltration at the site is complete (yes in decision block 106).

If infiltration is complete at the current site (yes in decision block 106) but infiltration is not complete (no in decision block 110), the tubular needle 12, 32 of the infiltration cannula 10, 30 is inserted into a new area of subcutaneous tissue 50. The process described above is performed until the infiltration process is complete (yes in decision block 110). This process can be repeated intermittently, for example every eight to twelve hours as described above.

As described above, multiple infiltration cannulas (e.g., can be used at once). Thus, a second cannula can be inserted (block 100) at the same time as a first cannula is being removed (block 108). Thus, the infiltration process need not be interrupted in order to reposition a single cannula.

Additional modifications and improvements of the present invention may also be apparent to those of ordinary skill in the art. Thus, the particular combination of parts described and illustrated herein is intended to represent only a certain embodiment of the present invention, and is not intended to serve as a limitation of alternative devices within the spirit and scope of the invention.

What is claimed is:

1. An infiltration cannula for use in an infiltration procedure, the infiltration cannula comprising:
   a tubular needle having a plurality of apertures disposed in a pattern and distributed over a distal 33% or more of the tubular needle, the apertures being configured to infiltrate a multi liter amount of fluid into subcutaneous tissue of a patient, a proximal portion of the tubular needle being devoid of apertures to prevent leakage or the fluid from the needle to outside of a patient;
   a hub configured to be held by a person performing the infiltration procedure, the hub having a first end and an opposing second end, the first end being attached to the proximal end of the tubular needle, the second end comprising a connector for receiving the fluid to be infiltrated into the subcutaneous tissue of the patient, the connector being in fluid communication with the hub and the tubular needle; and
   a continuous flow liquid pump connectable to the connector of the hub and operative to continuously deliver a multi liter amount of the fluid through the hub and the tubular needle.

2. The infiltration cannula of claim 1 wherein the infiltration pump is a peristaltic pump.

3. The infiltration cannula of claim 1 wherein the infiltration procedure is performed in conjunction with a liposuction procedure.

4. An infiltration cannula for use in an infiltration procedure, the infiltration cannula comprising:
   a single tubular needle having a plurality of apertures: disposed in a pattern and distributed over a distal 33% or more of the tubular needle, each of the plurality of apertures being about equal in size to the other apertures of the plurality of apertures, the apertures being configured to infiltrate a multi liter amount of fluid into subcutaneous tissue of a patient, a proximal portion of the tubular needle being devoid of apertures to prevent leakage of the fluid from the needle to outside of a patient;
   a hub configured to be held by a person performing the infiltration procedure, the hub having a first end and an opposing second end, the first end being attached to the proximal end of the tubular needle, the second end comprising a connector for receiving the fluid to be infiltrated into the subcutaneous tissue of the patient, The connector being in fluid communication with the hub and the tubular needle.

* * * * *